(12) United States Patent
Schmidt et al.

(10) Patent No.: US 7,322,970 B2
(45) Date of Patent: Jan. 29, 2008

(54) LIQUID HANDLING MEMBER WITH INNER MATERIALS HAVING GOOD CREEP RECOVERY AND HIGH EXPANSION FACTOR

(75) Inventors: Mattias Schmidt, Idstein (DE); Bruno Johannes Ehrnsperger, Frankfurt (DE); Fred Desai, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 458 days.

(21) Appl. No.: 10/168,877

(22) PCT Filed: Dec. 20, 2000

(86) PCT No.: PCT/US00/34742

§ 371 (c)(1),
(2), (4) Date: Nov. 26, 2002

(87) PCT Pub. No.: WO01/45614

PCT Pub. Date: Jun. 28, 2001

(65) Prior Publication Data
US 2003/0208137 A1 Nov. 6, 2003

(30) Foreign Application Priority Data
Dec. 23, 1999 (EP) ..................................... 9912593

(51) Int. Cl.
*A61M 1/00* (2006.01)

(52) U.S. Cl. ...................... 604/540; 604/313; 604/317; 604/327

(58) Field of Classification Search ........ 604/540–544, 604/313, 317–346
See application file for complete search history.

(56) References Cited

U.S. PATENT DOCUMENTS

| 4,320,743 A |   | 3/1982 | Allen |
|---|---|---|---|
| 4,394,930 A | * | 7/1983 | Korpman ................. 220/62.18 |
| 4,798,603 A | * | 1/1989 | Meyer et al. ................ 604/378 |
| 4,853,164 A | * | 8/1989 | Kiang et al. ................ 264/470 |
| 5,002,541 A | * | 3/1991 | Conkling et al. ........... 604/319 |

(Continued)

FOREIGN PATENT DOCUMENTS

WO    WO 00/00129 A1    1/2000

(Continued)

*Primary Examiner*—Tatyana Zalukaeva
*Assistant Examiner*—Michael G Bogart
(74) *Attorney, Agent, or Firm*—Laura L. Whitmer; George H. Leal; Jay A. Krebs

(57) ABSTRACT

The present invention is a deformable liquid handling member, having an inner region circumscribed and hermetically sealed by a wall region, which comprises a membrane assembly to separate a first zone outside of the member from a second zone within the inner region of the member. Thereby, the second zone is connected to a suction source capable of receiving liquid, and the first zone is positioned in liquid communication with a liquid releasing source during its intended use. The membrane assembly is capable of maintaining a pressure differential between the second zone and the first zone without permitting air to penetrate from said first zone to said second zone. Further, the inner region comprises an inner material, which has a volume expansion factor of more than 3, preferably 5, more preferably 10, and can have a creep recovery of more than 60%, preferably more than 90%.

17 Claims, 4 Drawing Sheets

U.S. PATENT DOCUMENTS

| | | | |
|---|---|---|---|
| 5,674,216 A * | 10/1997 | Buell et al. | 604/385.27 |
| 5,678,564 A | 10/1997 | Lawrence et al. | |
| 5,911,222 A | 6/1999 | Lawrence et al. | |
| 6,497,689 B1 * | 12/2002 | Schmidt et al. | 604/385.01 |
| 6,811,842 B1 * | 11/2004 | Ehrnsperger et al. | 428/34.1 |
| 6,849,065 B2 * | 2/2005 | Schmidt et al. | 604/313 |
| 2007/0135786 A1 * | 6/2007 | Schmidt et al. | 604/380 |

FOREIGN PATENT DOCUMENTS

| | | |
|---|---|---|
| WO | WO 00/00143 A2 | 1/2000 |
| WO | WO 00/00406 A1 | 1/2000 |
| WO | WO 00/00702 A1 | 1/2000 |

* cited by examiner

LIQUID HANDLING MEMBER WITH INNER MATERIALS HAVING GOOD CREEP RECOVERY AND HIGH EXPANSION FACTOR

BACKGROUND/PRIOR ART

Liquid handling systems comprising a membrane are known in the art. For example, U.S. Pat. No. 5,678,564 discloses a liquid removal system designed to permit liquid removal through the use of an interface device. The interface device is provided with a membrane which has and is capable of maintaining a vacuum on one side so that when liquid contacts the opposite side of the membrane the liquid passes through the membrane and is removed from the interface device by a maintained vacuum to a receptacle for disposal. Such a system is described to be useful as a female external catheter system. Also, in PCT application US99/14654 various desired properties for materials inside such interface devices are described, with particular embodiments showing collapsible inner materials.

Yet, there is a need for materials exhibiting improved properties with regard to maximizing the functionality especially over longer storage and/or use periods Thus the present invention aims at providing liquid handling member comprising inner materials with good creep recovery, low minimum liquid loading whilst maintaining functionality, and high maximum loading whilst maintaining functionality.

SUMMARY

The present invention is a deformable liquid handling member, having a inner region circumscribed and hermetically sealed by a wall region, which comprises a membrane assembly to separate a first zone outside of the member from a second zone within the inner region of the member. Thereby, the second zone is connected to a suction source capable of receiving liquid, and the first zone is positioned in liquid communication with a liquid releasing source during its intended use. The membrane assembly is capable of maintaining a pressure differential between the second zone and the first zone without permitting air to penetrate from said first zone to said second zone. Further, the inner region comprises an inner material, which has a volume expansion factor of more than 3, preferably 5, more preferably 10, and a creep recovery of more than 60%, preferably more than 90%.

Preferably, the inner material has an net uptake value of more than 6.5 g/g in the horizontal Surge Capacity test, and more than 5.5 g/g in the vertical Surge Capacity test. The inner material further comprises a creep resistant material having an elastic modulus of at least 10 MPa, an elongation at break of at least 60%, compression set less than 25%, and can maintain these values after accelerated aging for 3 days at 60° C.

A liquid handling member according to the present invention can be constructed by using repeating geometric units, which can be positioned between a first and a second support layer, arranged in an essentially parallel configuration extending in x-/y-direction perpendicular to their thickness along the z-direction at a distance H to each other, and a spacer layer having a material thickness significantly smaller than its x-/y extension, which is arranged and attached in a non-parallel orientation to and between said support layers, whereby the distance H of said support is greater than the thickness b of the spacer layer.

In a particular embodiment, the present invention comprises a multiplicity of spacer layers.

In a particular embodiment, the present invention comprises an inner material with a spacer layer arranged in corrugations, pleats, folds, walls, tubes, spheres, semishperes, which can be continuous or not.

The inner material spacer layer is preferably made of elastomeric materials, such as vulcanized polyurethane, and chemically cross-linked rubber, preferably SBR or Isoprene rubber or natural rubber, and the inner material support layer materials can be woven or nonwoven such as made from Nylon, or apertured films..

DETAILED DESCRIPTION

In the context of the present invention, a "liquid handling member" is considered to be a device, wherein a liquid is penetrating through a membrane by a driving force such as a suction like a vacuum. If this member is connected to a liquid delivery source, or liquid receiving sink, thus forming a "liquid handling system", this can be used in applications such as for—but without being limited to—receiving body liquids. In such applications, the liquid to be transported will be generally water based, such as body liquids like urine. It will be apparent to the skilled person, that the present invention is not limited to such applications, but that it can be readily re-applied to other liquids such as oily substances as disclosed in PCT applications US 99/14644 or US 99/14645.

Figure 1A:
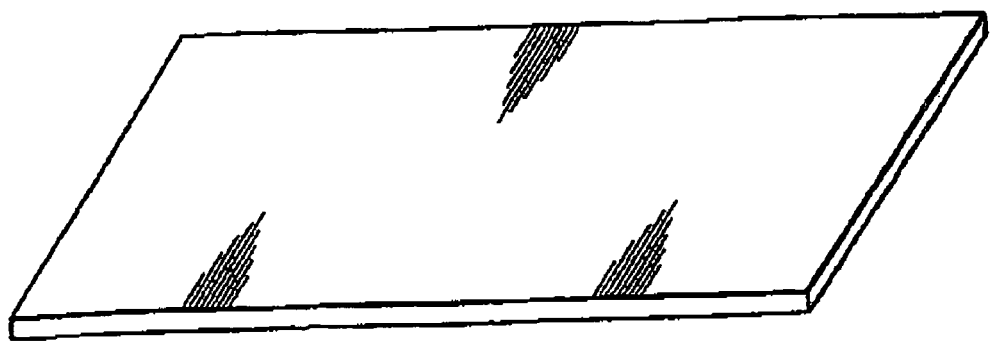
FIG. 1A is a schematic representation of suitable materials.
Figure 1B:
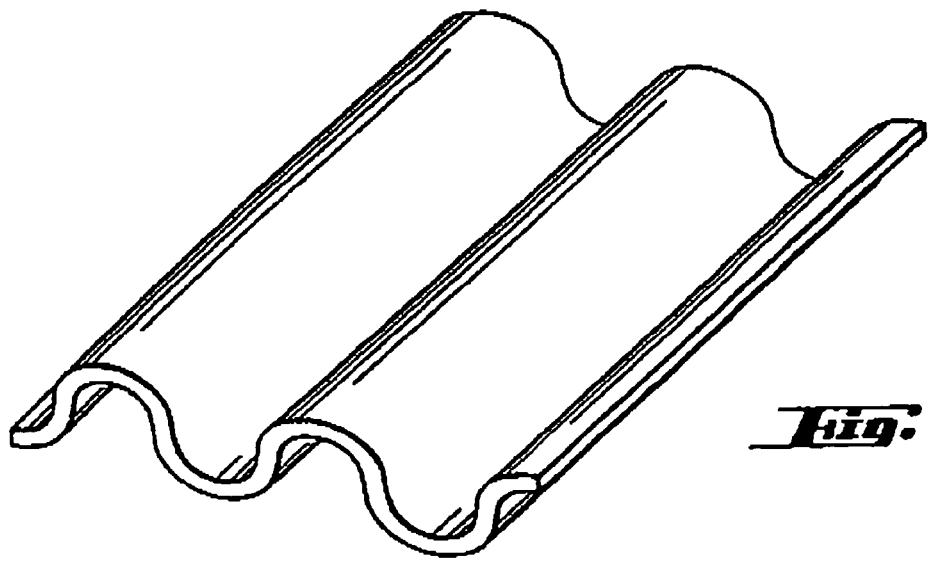
FIG. 1B is another embodiment of the present invention.
Figure 1C:
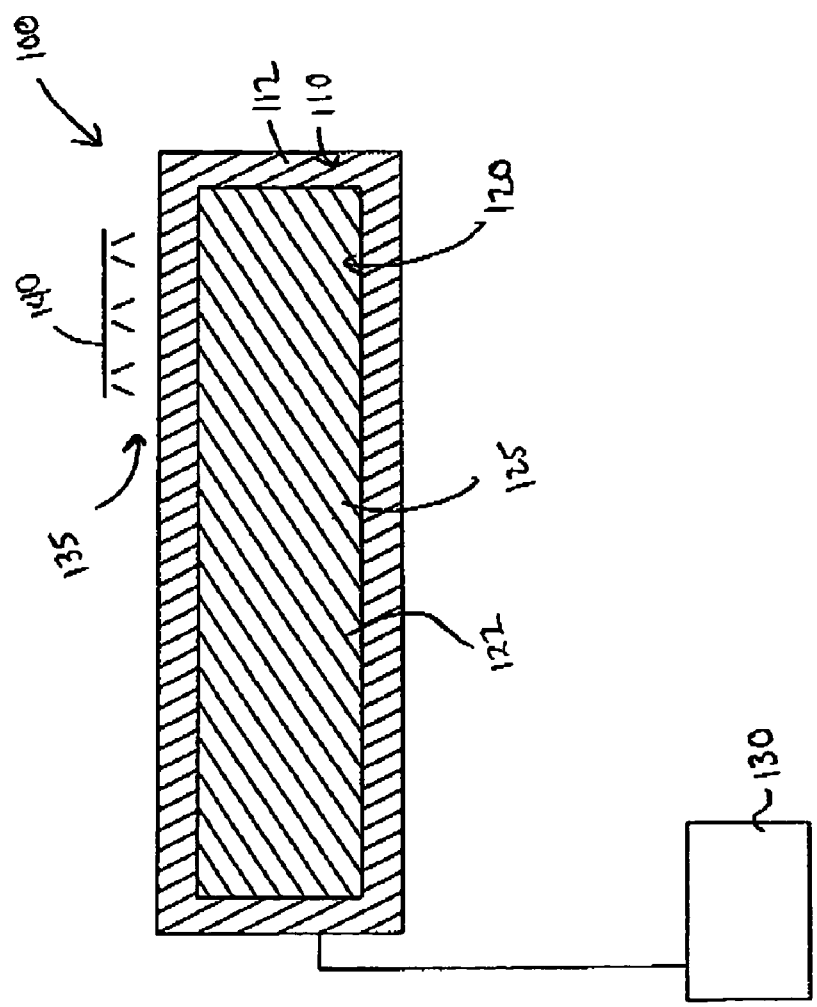
FIG. 1C is a cross sectional view showing a liquid handling member constructed in accordance with the present invention.

As shown in FIG. 1C, a deformable liquid handling member 100, constructed in accordance with the present invention, has an inner region 120 circumscribed and hermetically sealed by a wall region 110, which comprises a membrane assembly 112 to separate a first zone 135 outside of the member 100 from a second zone 125 within the inner region 120 of the member 100. The second zone 125 is in liquid communication with a suction source 130 capable of receiving liquid, and the first zone 135 is positioned in liquid communication with a liquid releasing source 140 during its intended use. The membrane assembly 112 is capable of maintaining a pressure differential between the second zone 125 and the first zone 135 without permitting air to penetrate from said first zone 135 to said second zone 125. Further, the inner region 120 comprises an inner material 122, which has a volume expansion factor of more than 3, preferably 5, more preferably 10, and a creep recovery of more than 60%, preferably more than 90%.

Such systems function by the principle that certain membranes under certain conditions can be permeable to liquids, but not to gases like air, as long as the "potential differential" such as the pressure differential between the two sides of such a membrane does not exceed a certain value, which is characteristic for a given material and given liquid in the pores of the material—the "bubble point pressure". This latter is often expressed in "height of water column" which corresponds to the pressure exerted by such a column on the material under normal gravity conditions.

For aqueous liquids, the material for the membrane is preferably hydrophilic and has a pore size of a diameter of about 5 to about 30 μm, more preferably about 10 to 20 μm. Once the membrane has been wetted it will support a suction pressure typically corresponding to about 12.5 cm to about 150 cm height of a water column without permitting air to pass therethrough. Thus, if suction is applied to one side of a wetted membrane, liquid contacting the membrane on the other side will be drawn by the suction through the membrane to the other side of the membrane, from where it can further be removed, for example by being sucked by means of a vacuum through a drain tube to a reservoir. As long as the filter material or membrane remains wet, air does not pass through the filter and suction is maintained without active pumping. If too much suction (too high vacuum) is applied to the membrane, there is a risk that the bubble point of the membrane will be surpassed and there will be no liquid in one or more pores of the membrane, thereby allowing air or gas to penetrate through, which can lead to a loss of the vacuum, and of the liquid handling functionality. Thus the amount of vacuum should approach as close as possible—but not exceed—the bubble point.

In such a system, the membrane needs to be "hermetically sealed" to the other elements, which means that a gas (and especially air) can neither pass from the outside environment to the inside of the member, when the membrane is saturated with liquid, as long as the pressure differential does not exceed the bubble point pressure.

This hermetic sealing can be achieved by only using membrane materials, and appropriately sealing them to each other to close the system. In addition to the membrane materials, there may be used liquid and vapor impermeable walls, such as for sealing areas where no membrane functionality is required or desired. Then, the membranes must also be "hermetically" connected to these wall regions.

The membrane of the member needs to maintain a certain degree of wetness, so as to maintain the pores filled with liquid, even -under suction vacuum, and/or evaporation conditions. As described for example in U.S. Pat. No. 5,678,564, the membrane material can be prewetted during manufacture. This may be done by any suitable liquid having preferably a low vapor pressure. Glycerin has been proposed as a prewetting agent because it has a significant smaller propensity for drying out by evaporation and will generally support the vacuum until the first wetting during use.

Generally, such systems can exhibit relatively high liquid transport rates. Thereby, it has been found useful to consider liquid "flux" through the system, expressed in flow of liquid per unit area of the system, e.g. [ml/sec/m$^2$]

In particular for applications where a low bulk is desired or required before its intended use (i.e. after manufacturing, and during shipment and storage, or in case of absorbent articles, such as external catheters, during wear time but before or after the loading phase), the materials in the inner regions are preferred to be compressible or collapsible during this phase so as to provide small volume and preferably also low weight, and to be expandable during the actual liquid handling step.

Similarly, it further can be advantageous, if the liquid handling member not only provides a high flux transport functionality, but that it has a certain buffer capacity. For example, if the total liquid handling system comprises a liquid storage member which has a relatively slow rate for receiving liquids, the liquid handling member can quickly receive gush volumes, and temporarily store these to release the liquid at a slower rate to the liquid storage member.

Henceforth, it can be very beneficial to have liquid handling members which are deformable. This has to be seen in the context of the intended application, i.e. these members should be able to adopt their overall shape to or during in-use conditions. In particular, when such members are applied for hygiene articles, they should conform to the body contours under normal forces as occurring during use. This is considered to be an important advantage over members having stiff elements, such as may be required to withstand deformation forces as can result from applying a vacuum suction to the member, such as described in U.S. Pat. No. 5,678,564.

A deformable member can be and preferably is deformable in its thickness dimension as described in further detail by having collapsible or expandable materials encased by a flexible casing. A deformable member can be and preferably is bendable in the x- and/or y-direction, i.e. perpendicular to its thickness direction.

Whilst it will be apparent to the skilled person to distinguish stiff structures, such as the shells as described in the already mentioned U.S. Pat. No. 5,678,564, deformable structures can be assessed by the bending test, as described in the test method section, preferably exhibiting buckling force values of less than 1 N, preferably less than 5 N, and more preferably less than 3 N or even less than 1 N.

Materials useful for application as inner materials of a liquid transport member in general have been described in PCT applications US 98/13497, generally exhibiting a high porosity and permeability. Therein, fibrous members are described using high-loft non-wovens, e.g., made from polyolefin or polyester fibers. Other suitable materials described therein are porous, open celled foam structures, such as polyurethane reticulated foams, cellulose sponges, or open cell foams as made by the High Internal Phase Emulsion Polymerization process (HIPE foams).

Alternatively, suitable properties could be achieved by circumscribing voids by certain structures, such pipes, or bundles, or by other "space holders", such as springs, spacer, particulate material, corrugated structures and the like.

Such materials have the ability to be compressed during transport from the manufacturing site to the user in a relatively thin (or low-volume) state, and upon application such materials can be activated, such as upon contact with the source liquid, to increase their volume so as to satisfy the void and permeability requirements.

Thus, one important property of such materials is their minimum liquid loading capacity, i.e. the minimal amount of liquid, which has to be retained in these members without losing their membrane and liquid transport property. The lower this value is, the less material needs to be transported.

At the same time, it is important, that the materials useful in such application have the ability to receive large amounts of liquid, i.e. have a high maximum loading capacity. Such a high capacity is not only beneficial for the interim storage aspect, but also indicates a relatively open structure, which is linked to the permeability of the material within the member.

This maximum loading capacity can be somewhat different according to the mechanism of loading, for example, for horizontal loading versus vertical loading, and as reflected in respective testing arrangements for the horizontal and vertical surge capacity, as described hereinafter.

Thus, the minimum loading capacity and the maximum surge capacity values determine the maximum net uptake, i.e. the maximum amount of fluid, as the difference between the two values.

When basing this net uptake capacity on the amount of material, the expansion factor can be determined. For aqueous liquids with a density of about 1.0, this expansion factor can be expressed as volumetric expansion factor (VEF), which also corresponds to the volume increase of the member upon activation. Thus, the VEF for a fully wetted strucure is the value of the volume of the liquid in the expanded state divided by the volume of the liquid in the compressed state.

It has now been found, that with an increase in expansion factors also the mechanical stress to which the materials are exposed, in significantly increasing, and that materials can lose their ability to regain their original volume if exposed to such compression forces for an extended period.

An extended period can be as short as several hours, but—for example when considering shipment and storage of manufactured articles, before these reach the user—can be several months.

A simple way to express creep is to measure the ability of a material to re-gain its caliper, after being submitted to compressive forces, such as a load or pressure applied to the material, for an extended period of time.

Creep can be measured on TA Instruments' (New Castle, Del., US) Dynamic Mechanical Analyzer, DMA 2980. In this test, a constant compressive stress is applied to the sample and the resulting strain is measured as a function of time. After a set time, the stress is removed and the strain (recovered caliper) is measured a s a function of time.

Coinciding with deformation of the material, an impact of pore size and porosity with the compression aging can be observed, such that the porosity can be reduced, and/or average pore size, and/or permeability of the material.

Particularly suitable materials exhibit a high ratio of porosity when expanded compared to collapsed or compressed. Whilst for example conventional polyurethane foams exhibit a porosity of 95% or more when being uncompressed, this is reduced to about 85% such as when exposed to a pressure of about 8950 Pa (about 1.3 psi). Preferred structures as described hereinafter, can be compressed to a porosity of less than 50%, more preferred ones to less than about 30% when exposed to a pressure of about 8950 Pa (about 1.3 psi), even when exhibiting a porosity of 90% or even 80% without applied pressure.

Henceforth, the materials suitable for being used in the present invention need to have carefully balanced properties with regard to the ones as described above.

For example, conventional PU foams, such as exemplified in the PCT application US 98/13497 do not meet the creep requirements, and further exhibit too high minimal loading values, and consequently too low volume expansion factors.

Materials suitable for the present application have the following properties, as can be evaluated by the respective test as described hereinafter: First, a net uptake value of at least 5 g/g, preferably at least 7 g/g, more preferably more than 10 g/g; second, a volume expansion factor of at least 3, preferably at least 5, more preferably more than 10; and thirdly a creep recovery value of at least 60%, preferably 90% even more preferably more than 95% after 22 hours aging under 8950 Pa (1.3 psi).

For applications in the hygiene field, such as for absorbent articles, it is preferred, that the material has an initial wet weight for 75 ml gush loading of less than 80 g, preferably less the 50 g, even more preferably less than 40 g.

Whilst the materials useful for the present invention can be made from various structures, it has been found that particularly useful materials can be constructed as "organized structures"—with repeating geometric cells.

The term "organized structures" relates to material composites, which combine materials in particularly effective designs, which will provide significantly different properties than the "precursor" materials alone. A well known example for such structures is the corrugated cardboard , where relatively thin and flexible paper sheets are combined into a much more rigid structure. The principles of such structures are exploited for the present invention, whereby, however, particular consideration has to be given to particular properties and parameters.

A particularly preferred execution uses repeating geometric units, which can have two dimensional repeating cell units (as the repeating cross-sections for corrugations, pleats or folds), or can have three-dimensional repeating cell units (such as for having a sheet material with protuberances extending from both surfaces, such as result from particular embossing).

Such repeating geometric cells can have smooth transitions from one cell to the next—such as the well-known card-board corrugations. Alternatively, there can be certain discontinuities between adjacent cells, such as when there are folds or in the connection sections. Also, if the structure consists of several materials, not all of these need to be present throughout the structure, but can be restricted to certain parts of the structure.

For ease of explanation, the following explanation will consider corrugated structures, but this should not be considered in any way as a limiting embodiment. For such idealistic structures, it is assumed, that the geometric unit cell consists of two horizontal support layers connected and spaced apart by vertical walls. For non-ideal pleated or corrugated structures, these vertical walls can be inclined, can contact neighboring walls (such as forming a V or M or a "Leporello" structure) or can be rounded such as like connecting semi-circular elements, or having sinusoidal shape. Also, the inner materials can be in the form of tubes, spheres, semi-spheres, etc. as long as there is provision for liquid to transfer easily through such structures, such as by keeping the ends of pipes open, or having apertures in the walls of spheres.

For all of these structures, particularly the following geometric parameter will be relevant for the properties of the structure. For the walls, the key parameters are the thickness, the height, the distance between the walls, their shape (vertical, straight, curved, circular, sinusoidal, . . . ), their connectedness, and in case of discontinuous strips, their respective distance. For the support layers, the key parameters are the distance of the upper and lower support layers; the thickness; and their arrangement (continuous, stripes, . . . ).

In addition to these geometric requirements, the materials used in the walls and/or support materials can be assessed for their most critical properties, namely their "stiffness requirements", such as can be expressed by the elastic modulus. Preferred materials exhibit a high elastic modulus, as this allows minimized material usage. Another parameter is the elongation at break, which for preferred material should be at high values for improved crack resistance, such as during use, or during folding. Further, the creep and stress relaxation must be low to allow good storage.

Figure 1D:
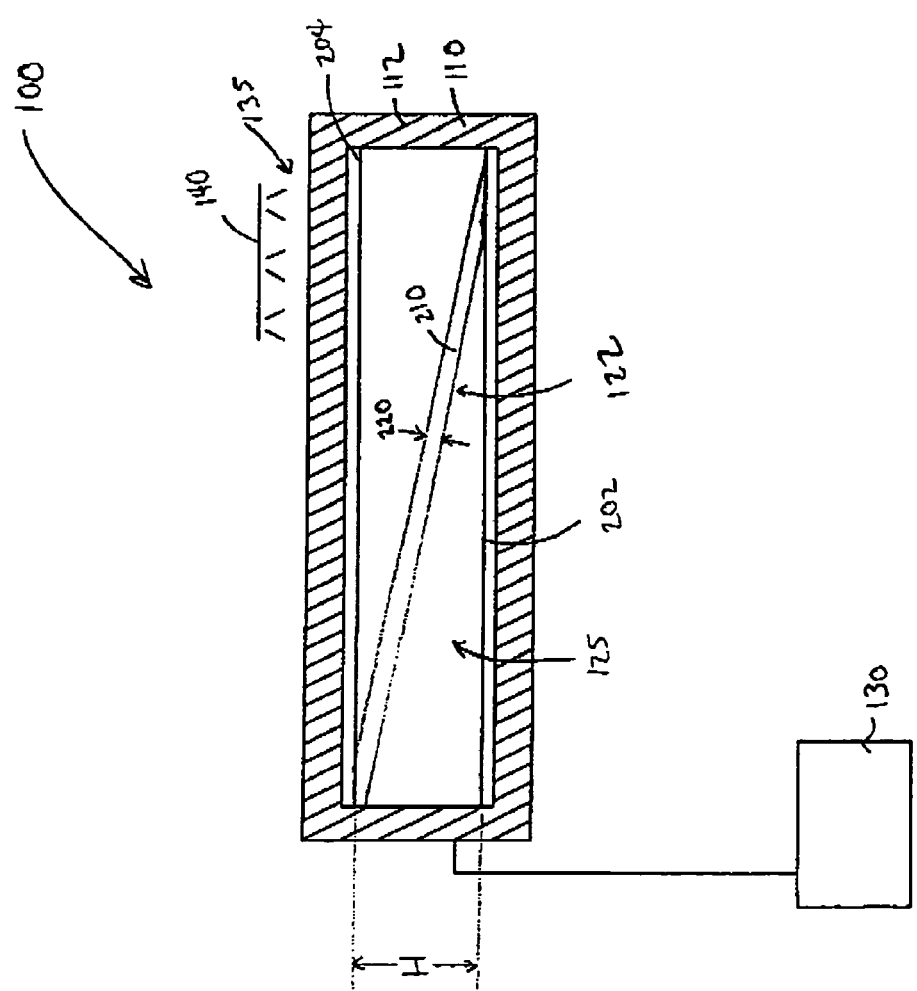
FIG. 1D is a cross sectional view showing another embodiment of a liquid handling member constructed in accordance with the present invention.

As shown in FIG. 1D, in some embodiments, the inner material 122 of the liquid handling member 100 may comprise first and a second support layers 202 and 204. The first support layer 202 and the second support layer 204 can be arranged in an essentially parallel configuration extending in x-/y-direction perpendicular to their thickness along the z-direction at a distance H to each other. The inner region 120 may further comprise a spacer layer 210 having a material thickness 220 significantly smaller than its x-/y extension. The spacer layer 210 can be arranged and attached in a non-parallel orientation to and between said support layers 202 and 204, whereby the distance H of said support is greater than the thickness 220 of the spacer layer.

A particularly preferred execution with regard to material composition relates to the use of elastomerics for the wall materials, or other materials exhibiting a highly elastic behavior. Elastic behavior can be assessed by measuring creep recovery. In this test, the material is compressed under 8950 Pa (1.3 psi) pressure for i) 2 minutes at room temperature , ii) 22 hours at room temperature and iii) 3 days at 60° C. The material is allowed to recover under a 0.23 psi compression pressure at room temperature for 5 minutes. Creep recovery is the recovered caliper after long term compression normalized to the recovered caliper after 2 minute compression at room temperature.

The elastic behavior can be assessed by a simplified creep test as described in the method section, and should result in a creep recovery after 22 hrs at RT of not less than 60%, preferably no less than 80%, and more preferably no less than 90%, and most preferably no less than 95% or even more than 97%.

Further, the elastic modulus of the materials (also referred to as Young modulus) should exceed 5.0 MPa, preferably be more than 10 MPa, and even more preferably be even more than 15 MPa.

At the same time, the materials should exhibit a break elongation value of at least 60%, preferably more than 100%, more preferably more than 150%, and most preferably more than 200%.

Preferably, the elastic modulus and the break elongation values should be met after being aged under about 8950 Pa (about 1.3 psi) for at least 22 hours at room temperature. Of course, other requirements may be imposed by the intended use conditions, such as safety or comfort considerations for the user in certain hygiene applications.

Another preferred execution with regards to material composition relates to the use of creep resistant, very thin, high modulus materials for the walls,. These materials need to be thin enough so that when the material is bent, the local strain along a major portion of the wall is within elastic limits.

When considering creep resistant elastomeric materials, the following particular embodiments have been found suitable:

i) chemically crosslinked rubbers, like isoprene rubber, styrene butadiene rubber (SBR), and natural rubber; such as produced by Akron Rubber Development Labs. (ARDL), Akron, Ohio (PN 36697, isoprene rubber: code ARDL-F, SBR: code SBR, and natural rubber: code DPNR-1A)

ii) chemically/physically crosslinked polyurethanes like room temperature vulcanized (RTV) polyurethanes made by mixing prepolymers obtained from BJB Enterprises (Tustin, Calif.).

iii) creep resistant, very thin, high modulus materials in the form of filaments, yarns, ribbons, films, sheets, such as a) liquid crystalline polymers like i) aromatic polyamides or aramids like Kevlar and Nomex (Du Pont) and Technora (Teijin, Japan), ii) aromatic polyesters like Vectra fibers (Celanese), and iii) aromatic polyimides; b) polyesters with improved creep properties, e.g. poly-1, 4-cyclohexylene-dimethylene terephthalate (PCDT, Kodel fibers), c) nylons with improved creep properties, d) stainless steel, and e) glass fibers.

Generally, suitable support structures should have a low extensibility so as to maintain the corrugations.

Such support structures can be liquid impermeable, if they do not impede the liquid handling properties of the structure, for example by not being continues, but only nets, open meshes, NW and the like or strips, struts, bands or the like. Alternatively, suitable support structures can also be liquid permeable, and can have a liquid handling functionality, such as being the membrane materials of liquid handling member Particularly suitable support structures are woven meshes with mono- and/or multi-filament yarns, or apertured films, or non-wovens, or membrane materials, such as Nylon meshes, as available under the designation 03-150/38 from Sefar, Switzerland.

The distance between the support layers may be between 0.05 mm and 30 mm under no restraining force. The distance between the support layers may be between 0.05 mm and 30 mm under 8950 Pa (1.3 psi).

The support structure and the wall materials can be bonded to each other by various conventional ways, such as glues or thermal/heat bonding in various patterns, though care should be taken, that none of the relevant properties are unduly affected.

Whilst the above description relates to essentially flat or sheet-like structures, the same principles apply to three-dimensionally shaped structures, which—for example—can be constructed by combining two or more of these structures on top of each other. Thereby, the design principles remain unchanged, whereby the wall materials of two different levels can have one and the same support sheet, i.e. one being attached to one side of the support sheet, and the other to the opposite side.

Such two- or multi layer structures can further have the same construction, or can have different properties in different levels. Such a structure also can have the same x-and/or y-extension for all sub-layers, and thus create a "macro-layer" or the sub-layers can have different extensions, such that a irregularly shaped volume for the member can result.

Depending on the intended application, it may be particularly desirable for the combined structure (i.e. support and wall elements combined) to exhibit certain deformation properties. In particular, in addition to the compressibility requirements for the structure (which essentially is along the thickness direction of the structure), the flexibility and deformability in x- and in y-direction can be of importance. For certain applications, the structure should be very flxible and deformable, such as when used in otherwise pliable or flexible articles, in particular when being used in hygine articles. For other applications, the deformability should not be too high, or the respective flexibility too low, so as to provide a certain structural integrity to the otherwise still deformable structure.

For hygiene applications, such a external catheter, or absorbent articles like disposable diapers the resulting structure should generally be quite deformable and pliable to comply with the body contours of the wearer, and/or to comply to change of the body contours during use, such as by movements or change of position. Such deformability and softness provides increased comfort during wear. As is well known softness is a subjective, multi-faceted property including components such as bending resistance, buckling resistance and coefficient of friction. As is also known the tensile properties of a material are also important as a predictor of softness. In particular, materials having a low tensile modulus and high elongation are desirable. However, as also well known from corrugated cardboards, the bending in x- or y-direction (i.e perpendicular to the thickness direction) can be impacted by the three.

Such deformability can be assessed by considering bending and buckling resistance. An especially desirable measure of the bending component of softness in the case of absorbent article core components has been found to be buckling resistance. As will be recognized by one of skill in the art, the corrugated structure as described in the above can assume an arcuate configuration such as when implemented into an absorbent article, and applied to the wearer, where it should conform to a wearer's anatomy. The Bulk Softness test described in the Test Methods section below uses resistance to compressive deformation of a sample having a controlled arcuate configuration as a measure of the softness of the sample. Suitably, a structure according to the present invention has a buckling force of less than about 10 N. Preferably, the buckling force is less than about 5 N, more preferably less than 3 N or even less than about 1 N.

In a particular embodiment, the ratio of the buckling force in x-direction to the buckling force in y-direction is more than 0.7 and less than 1.3.

When considering a preferred application of the present invention, namely the use of liquid handling members in hygiene articles, the used materials preferably are non irritating, or allergenic. Further, for such applications, the expected loading conditions for the article can be estimated, which can be total loads of 400 ml or more, delivered in gushes of 75 ml or more, with gush rates of 15 ml/sec or more. In order to allow liquid handling members to cope with such requirements, a sample structure can be constructed as follows:

A sheet of elastomeric of the type as described in the above (ARDL code: SBR, PN 36697) having a caliper of about 0.4 mm a Young modulus of about 7 Mpa; and a break elongation of about 100%), is prepared by being scissored into a 15 cm×14 cm piece. Its total weight and caliper are determined at various locations to allow meaningful averaging. The piece is cut into stripes of about 3 mm width. Two 5 cm×15 cm pieces of the nylon support 150 micron nylon mesh (03-150/38 from Sefar, Switzerland) and the respective weight and caliper are determined. Using rods of suitable size and material, such as Perspex or steel or wood, the elastomeric stripes are corrugated and the ends are fixed to a suitable support surface (e.g. benchtop) with tapes. Also, use tapes to keep the rods in place. Suitable corrugated structures were made using rods ranging in diameter from ⅛" to 5/16". For discontinuous corrugations, adjacent rubber corrugations are placed on the mesh spaced apart, such as having a gap of 9 mm between the stripes.

A thin layer of suitable adhesive, such as a cyanoacrylate adhesive commercially available under the trade designation "Super Jet Glue" (Carl Goldman Models, Chicago, USA), is put on the crests of the corrugation loops, thus bonding it to the nylon mesh.

Then, a conventional polyethylene film is put on top of the nylon mesh and a pressure of about 8950 Pa (about 1.3 psi) is applied for about 5 minutes. The weights and the films are removed, and the structure is allowed to air dry for about 1-3 hours under the controlled lab conditions.

Then, the structure is flipped over and the second support structure in form of a same nylon mesh is attached to the other side in the same way. Excess elastomer is trimmed off, and the weight and caliper of the inner material is measured.

The resulting structure has a structure height of about 6 mm, with about 1 repeating unit per cm, whereby the corrugated elements cover about 25 to 50% of the total area..

Test Procedures

Unless otherwise noted, the tests are carried out under standard laboratory conditions of 22° C. and 50% relative humidity, with distilled or deionized water as test liquid.

Caliper

Caliper is measured by an caliper gauge such as Ono Sokki gauge model no. EG-225 (0.001~25 mm), Ono Sokki, Japan, having a foot diameter of 1" and foot weight of 40 g.

Caliper is measured at 0.23 psi and 1.3 psi compression pressures. These compression pressures are applied by placing appropriate weights directly on the sample and then measuring the total caliper of the sample and the weights. This protocol was necessary for the following reason. When the corrugated structure collapses, there is shear between the top and bottom support plates. Hence, any measure of caliper under pressure had to provide for the plates to slide horizontally.

The following weights were used to get the appropriate compression pressure (2 cm×4.5 cm sample):

⅛" Lexan plate: 36.9 g, 3.3 mm×10 cm×10 cm

⅜" Lexan plate: 69.7 g, 9.1 mm×8.3 cm×8.3 cm

⅜" SS plate: 776 g, 9.5 mm×10 cm×10 cm

Gauge foot: 40 g 0.23 psi: ⅛" Lexan+⅜" Lexan+gauge foot 1.3 psi: ⅛" Lexan+⅜" SS+gauge foot.

Creep Recovery

This tests aims at determining the resistance to permanent deformation under an external load, whereby the load is applied in the direction as would correspond to in-use conditions.

A sample is prepared by cutting a 2 cm wide and 4.5 cm long piece out of the material.

A weight is prepared to create 9080 Pa (1.3 psi) pressure such as by using 10 cm×10 cm×⅜" stainless steel plate covered 10 cm×10 cm×⅛" LEXAN layer on the material oriented side, the plate and the LEXAN weighing 853 g. The weight is placed onto the upper surface of the test material, and allowed to compress the material for 2 minutes, in further test runs with further samples for 30 minutes, and 22 hrs at standard room conditions of 25° C. temperature and 50% RH. A fourth test specimen can be tested for 3 days at 60° C.

Upon removal of the weight at the end of the compression period, the recovered caliper is measured by an caliper gauge such as described above as a function of time for 5 minutes.

The creep is expressed in percent of recovery normalized by the recovery after 2 minutes load.

Minimum Liquid Loading

This is the amount of liquid in a liquid handling member at the point where the member looses it functionality, when liquid is sucked out of the member.

In order to measure this value for an inner material, a sample of 5 cm by 15 cm at the uncompressed thickness of the inner material is hermetically sealed in a suitable membrane material such as the type 03/10-5 or 03/20-14 of Sefar, Switzerland.. The weight of the inner material as well as of the composite is recorded as "dry weight".

This composite is saturated under free swell conditions with water at room temperature, by immersing it therein, whilst allowing air to escape via at least one corner which is kept dry until all the remainder is filled. The weight of the composite is recorded as "saturated weight".

The composite is placed on a stack of 20 sheets of filter paper of about 10 cm by 10 cm (4" by 4")(such as Whatman Type 989 under a compression load of 413 Pa (0.06 psi), such that water is desorbed until air is sucked through the membrane. If the desorption paper is too highly loaded, it can be replaced by fresh filter paper. This desorption can be aided by first squeezing out a part of the liquid between two plates such as 20 cm by 20 cm Perspex or Lexan plates, which can be manually compressed, carefully avoiding localized pressurizing, and too high pressure.

As soon as the first air bubble enters into the system, the composite is removed from the desorption paper, and the weight as is recorded as "minimum liquid loading weight".

The "minimum liquid loading" of the inner test sample is the least amount of liquid remaining in a compressed material expressed in the units of grams of liquid per gram of dry material..

Surge Capacity

The surge capacity of an inner material or member describes the amount of liquid which a member can receive, whereby this material or member is pre-loaded to a certain extent and prefilled and compressed to a certain degree. The test can be executed in two ways, namely when the sample is being positioned either essentially horizontally flat, or vertically.

For both approaches, an inner material—after determining its "dry weight"—is hermetically sealed into a suitable membrane, such as the Sefar material as described above.

The composite is saturated with liquid as above. Then, this composite is compressed either manually or by suitable tools such as automatic presses, or by being dried by suitable suction means such as the above described filter paper, until a certain amount of liquid remains therein (the "initial liquid loading" which needs to be higher (about 0.2 to 0.5 g/g ) than the above referred to "minimum liquid loading"). The corresponding weight is recorded.

The composite is then wrapped into a liquid impermeable, flexible film, such as conventional PE (Saran) film or bag or aluminum foil, and stored in the compressed state for 5 minutes.

Both tests can be repeated several times, as the surge capacity of suitable materials does not substantially change over multiple gushes.

Horizontal Surge Capacity

The compressed, unwrapped composite is placed on a suitable plate, such as made form Lexan or perspex, which is arranged at a 5° angle to the horizontal, and a load is applied corresponding to 1580 Pa (0.23 psi) by means of a further LEXAN plate and stainless steel plates. Liquid is delivered to the composite, such as by using a 50 ml pipette at a rate sufficiently slow to allow to be picked up until its saturation, which is recorded upon visual observation of liquid overflow. The composite is re-weighed, after surplus liquid has been removed (i.e. the overflow or other non-absorbed liquid). The Horizontal Surge Capacity is calculated from the amount of liquid picked up divided by the weight of the dry inner material, expressed in g/g (i.e. g liquid/per gram of dry inner material).

Vertical Surge Capacity

The compressed, unwrapped composite is immersed into a reservoir of test liquid, whereby the reservoir is placed on a scale, and the composite is hung from a separate support structure, being immersed into the reservoir by 5 mm.The weight change of the reservoir is recorded for 3 minutes, at least initially at least every 5 seconds. After 3 minutes, or 20 seconds respectively, the sample is removed from the reservoir, and reweighed to determine the Vertical Surge load.

The Vertical Surge Capacity is calculated from the liquid pick up divided by the dry weight of the inner material, and expressed in g/g.

Volume Expansion Factor

The Volume expansion factor is defined by the relative expansion of the inner material which corresponds to the liquid uptake in the above surge capacity tests. For aqueous liquids such as synthetic urine with a density of about 1.0 g/cm$^3$, the volume expansion factor corresponds to the gravimetric expansion factor.

Hence, for such systems, the volume expansion factor can be calculated by dividing the g/g liquid loading in the expanded state (after horizontal or vertical surge tests) by the g/g liquid loading in the compressed state (i.e. initial liquid loading Bulk Softness This method is intended to measure individual materials as well as structures comprising these materials. The method uses a tensile tester in compressive mode and a sample holder (FIG. 2) to measure the buckling force for a sample.

A suitable tensile tester is available from Zwick Company of Ulm, Germany as a Zwick Material Tester type 144560.

Figure 2:
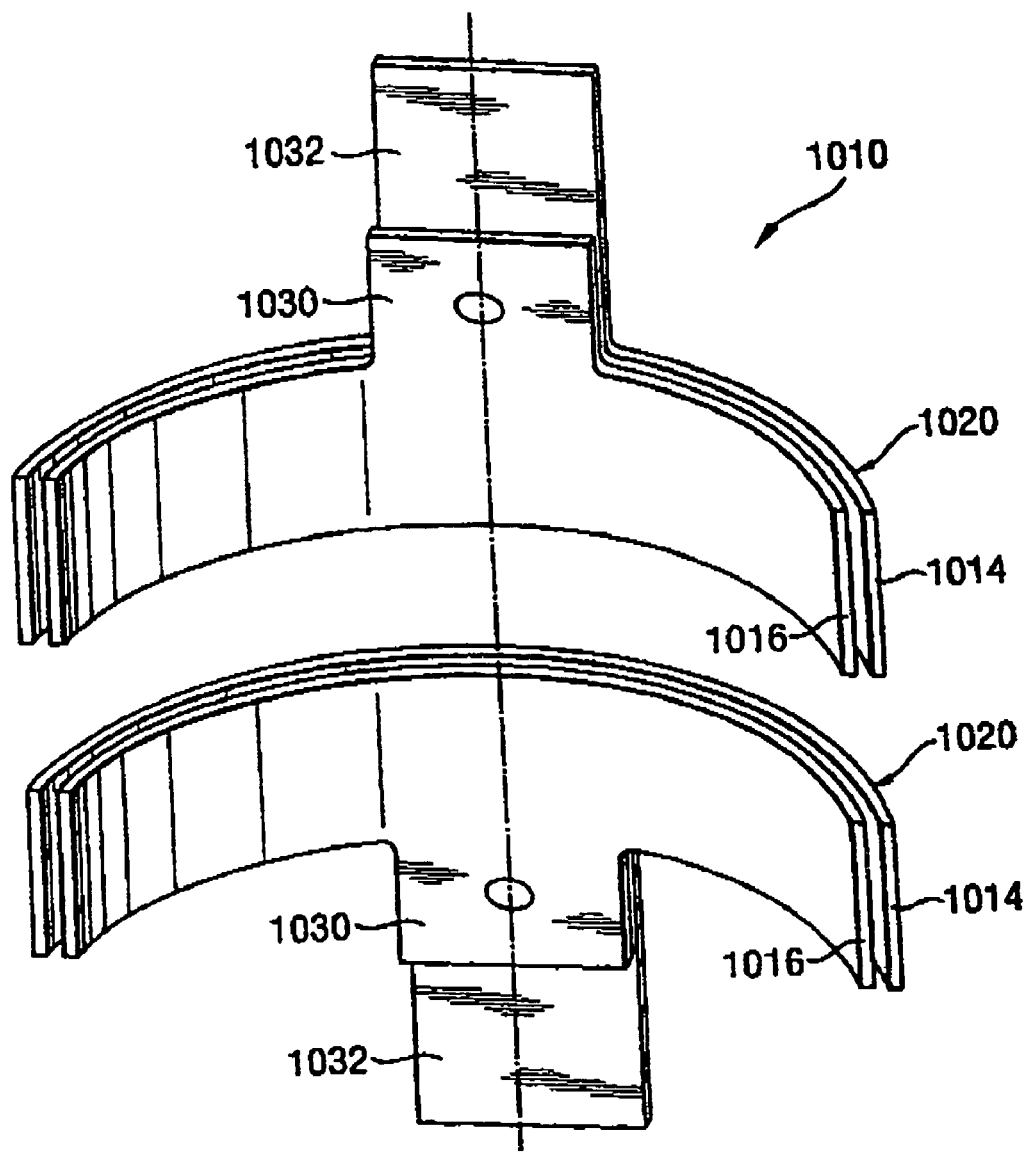
FIG. 2 shows the sample holder for the bulk softness test.

The sample holder 1010 for this test is shown in FIG. 2. As can be seen therein the sample is held between two curvilinear plates 1020 that have tabs (1030, 1032) 30 mm wide that extend upward 20 mm (front element, 1030) and 55 mm (rear element, 1032) so as to enable insertion of the sample holder 1010 into the jaws of the tensile tester. Readily the curvature of the outer element 1014 of the holder has a radius of 59 mm±1 mm with an arc length of 150 mm and the inner element 1016 has a radius of 54 mm±1 mm with an arc length of 140 mm. The equipment is designed to test various material thicknesses from 1 mm up to 10 mm. As will be recognized, sample holders of this type are necessary for both the upper and lower jaws of the tensile tester.

Prior to testing a sample is conditioned under controlled conditions (50% RH, 25° C.) for at least two hours. The sample is cut to 60 mm×150 mm (±2 mm per dimension). The sample dimensions, short side vs. long side, should be consistent with the bending axis orientation for which the test is executed, and can be aligned with the intended use in a finished product, whereby the y-axis generally corresponds to the left-right orientatin of the user, and generally to the width dimensin of the article, and the x-axis being perpendicular thereto. The operation is as follows:

1. The tensile tester is calibrated (in compressive mode) according to the manufacturer's instructions.
2. The compression rate is set to 200 mm/minute and the crosshead stop point to 30 mm.
3. A sample is inserted into the sample holder to a depth of 7 mm ±1 mm for each clamp set.
4. The tensile tester jaw separation is set so that the unconstrained portion of the sample is smooth and unbuckled. This corresponds to a spacing between the upper and lower portions of the sample holder of 46 mm.

5. The sample/sample holder assembly is inserted into the jaws of the tensile tester.
6. The tensile tester is operated in compressive mode to record a force/compression curve for each sample.
7. The buckling force for each sample is recorded, which is the force required to cause the sample to initially begin to bend. It is the initial peak force that is seen on the force compression curve before a relatively constant force plateau that is a measure of the bending resistance of the sample (bending force) and is expressed in Newton (N).
8. Repeat steps 5 to 7 for at least 5 samples for each structure tested and report the average and standard deviation of the buckling forc Compression Set Test This test is executed by following the instructions according to ASTM D-395-97 *(Standard Test Method for Rubber Property—Compression Set, Method B, with a compression time of 22 hours under a temperature of 60° C.

What is claimed is:

1. A deformable liquid handling member
  having a inner region circumscribed and hermetically sealed by a wall region, said wall region comprising a membrane assembly to separate a first zone outside of the member from a second zone within the inner region of the member,
  wherein said second zone is in fluid communication with a suction source capable of receiving liquid, and said first zone is positioned in liquid communication with a liquid releasing source during its intended use,
  wherein said membrane assembly is capable of maintaining a pressure differential between the second zone and the first zone without permitting air to penetrate from said first zone to said second zone,
  wherein said inner region comprises an inner material, wherein the inner material is an elastomeric material, said inner material having a volume expansion factor of more than 3;
  wherein said inner material comprises a first support layer and a second support layer, arranged in an essentially parallel configuration extending in x-/y-direction perpendicular to their thickness along the z-direction at a distance H to each other,
  and a spacer layer having a material thickness b significantly smaller than its x-/y extension,
  said spacer layer being arranged and attached in a non-parallel orientation to and between said support layers,
  and whereby the distance H of said support is greater than the thickness b of said spacer layer.

2. A deformable liquid handling member according to claim 1, wherein said inner material has a creep recovery of more than 60%.

3. Liquid handling member according to claim 1, wherein said inner material has a net uptake value of more than 6.5 g/g in the horizontal Surge Capacity test.

4. Liquid handling member according to claim 1, wherein said inner material has an net uptake value of more than 5.5 g/g in the vertical Surge Capacity test.

5. Liquid handling member according to claim 1, wherein said inner material exhibits said values after accelerated aging for 3 days at 60° C.

6. Liquid handling member according to claim 1 wherein the distance between said support layers is between 0.05 mm and 30 mm under no restraining force.

7. Liquid handling member according to claim 1 wherein the distance between said support layers is between 0.05 mm and 30 mm under 8950 Pa (1.3 psi).

8. Liquid handling member according to claim 1 wherein said inner material comprises a spacer layer arranged in corrugations, pleats, folds, walls, tubes, spheres, and semi-spheres.

9. Liquid handling member according to claim 8, wherein said corrugations are discontinuous.

10. Liquid handling member according to claim 1, wherein said spacer layer comprises material selected from the group of vulcanized polyurethane, and chemically cross-linked rubber.

11. Liquid handling member according to claim 1, wherein said support layer comprises creep resistant fibers.

12. Liquid handling member according to claim 1, wherein said spacer layer comprises creep resistant, thin, high modulus material.

13. Liquid handling member according to claim 1, wherein said support layer comprises elastomeric material.

14. A liquid handling member according to claim 1, comprising a multiplicity of spacer layers and support layers.

15. Liquid handling member according to claim 1, wherein said member exhibits a buckling force of less then 10 N, in at least one of the x- or- y-direction oriented perpendicularly to the thickness direction of the member, when submitted to the bulk softness test.

16. Liquid handling member according to claim 15, wherein the ratio of the buckling force in x-direction to the buckling force in y-direction is more than 0.7 and less than 1.3.

17. A deformable liquid handling member having an inner region circumscribed and hermetically sealed by a wall region, said wall region comprising a membrane assembly to separate a first zone outside of the member from a second zone within the inner region of the member, wherein the inner region comprises an inner material selected from the group consisting of chemically crosslinked rubbers, chemically crosslinked polyurethanes, physically crosslinked polyurethanes, and creep resistant high modulus materials;
  wherein said second zone is in fluid communication with a suction source capable of receiving liquid, and said first zone is positioned in liquid communication with a liquid releasing source during its intended use;
  wherein said membrane assembly is capable of maintaining a pressure differential between the second zone and the first zone without permitting air to penetrate from said first zone to said second zone;
  wherein said inner material comprises a first support layer and a second support layer, arranged in an essentially parallel configuration extending in x-/y-direction perpendicular to their thickness along the z-direction at a distance H to each other,
  and a spacer layer having a material thickness b significantly smaller than its x-/y extension,
  said spacer layer being arranged and attached in a non-parallel orientation to and between said support layers,
  and whereby the distance H of said support is greater than the thickness b of said spacer layer.

* * * * *

UNITED STATES PATENT AND TRADEMARK OFFICE
CERTIFICATE OF CORRECTION

PATENT NO.         : 7,322,970 B2
APPLICATION NO. : 10/168877
DATED                  : January 29, 2008
INVENTOR(S)        : Mattias Schmidt et al.

It is certified that error appears in the above-identified patent and that said Letters Patent is hereby corrected as shown below:

Title Page

Item (75), Inventors:, delete "Frankfort" and insert -- Bad Soder --.

Item (30), Foreign Application Priority Data, delete "9912593" and insert -- 99125930 --.

Column 1

Line 34, delete "a" and insert -- an --.

Line 49, delete "an" and insert -- a --.

Column 2

Line 12, delete ".." and insert -- . --.

Column 3

Line 41, delete "-"

Column 8

Line 8, delete "continues" and insert -- continuous --.

Line 13, after "member" insert -- . --.

UNITED STATES PATENT AND TRADEMARK OFFICE
CERTIFICATE OF CORRECTION

PATENT NO.       : 7,322,970 B2
APPLICATION NO.  : 10/168877
DATED            : January 29, 2008
INVENTOR(S)      : Mattias Schmidt et al.

It is certified that error appears in the above-identified patent and that said Letters Patent is hereby corrected as shown below:

Column 10

Line 13, delete "an" and insert -- a --.

Column 11

Line 2, delete ".." and insert -- . --.

Line 25, delete ".." and insert -- . --.

Signed and Sealed this

Fifteenth Day of July, 2008

JON W. DUDAS
*Director of the United States Patent and Trademark Office*